(12) United States Patent
Wu

(10) Patent No.: US 12,102,160 B1
(45) Date of Patent: *Oct. 1, 2024

(54) HEADGEAR WITH CURVED STRAPS FOR WELDING HELMET

(71) Applicant: TECMEN ELECTRONICS CO., LTD, Jiangsu (CN)

(72) Inventor: Ziqian Wu, Nanjing (CN)

(73) Assignee: TECMEN ELECTRONICS CO., LTD, Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/168,497

(22) Filed: Feb. 13, 2023

Related U.S. Application Data

(63) Continuation of application No. 16/442,390, filed on Jun. 14, 2019, now Pat. No. 11,576,454.

(51) Int. Cl.
  *A42B 3/08* (2006.01)
  *A42B 3/20* (2006.01)
  *A61F 9/06* (2006.01)

(52) U.S. Cl.
  CPC .............. *A42B 3/085* (2013.01); *A42B 3/20* (2013.01); *A61F 9/06* (2013.01)

(58) Field of Classification Search
  CPC .. A42B 3/085; A42B 3/20; A42B 3/08; A42B 3/04; A42B 3/14; A42B 3/142; A42B 3/145; A42B 3/147; A42B 3/066; A61F 9/06
  See application file for complete search history.

(56) References Cited

U.S. PATENT DOCUMENTS

| | | | |
|---|---|---|---|
| D131,153 S | 1/1942 | Jones | |
| 2,461,605 A | 2/1949 | Huntsman | |
| 3,041,622 A * | 7/1962 | Gurtowski | A42B 3/145 2/8.1 |
| 3,082,428 A | 3/1963 | Zbikowski | |
| 3,156,922 A * | 11/1964 | Anderson | A42B 3/14 2/419 |
| 4,843,642 A | 7/1989 | Brower | |
| 5,896,586 A * | 4/1999 | Freund | A42B 3/145 2/418 |
| 6,341,382 B1 | 1/2002 | Ryvin et al. | |
| 8,336,114 B1 * | 12/2012 | Lee | A42B 3/145 2/9 |
| D710,546 S | 8/2014 | Wu | |
| 10,588,373 B2 * | 3/2020 | Staudinger | A42B 3/08 |
| 2005/0010992 A1 | 1/2005 | Klotz et al. | |

(Continued)

*Primary Examiner* — Khoa D Huynh
*Assistant Examiner* — Uyen T Nguyen

(57) ABSTRACT

The present disclosure includes a headgear for a helmet. The headgear includes a front band, a back band, and an intermediate band comprising a plurality of intermediate band parts arranged between the front band and the back band. The plurality of intermediate band parts comprises first pair of band parts having a circular shape, the band parts of the first pair of band parts extending from and connecting on a first side of the headgear, a second pair of band parts having a circular shape, the band parts of the second pair of band parts extending from and connecting on a second side of the headgear, a first cross band part intersecting with and extending from the connection of the first pair of band parts, and a second cross band part intersecting with and extending from the connection of the second pair of band parts.

16 Claims, 7 Drawing Sheets

(56) References Cited

U.S. PATENT DOCUMENTS

| | | |
|---|---|---|
| 2007/0245467 A1 | 10/2007 | Lilenthal et al. |
| 2010/0050324 A1* | 3/2010 | Musal .................... A42B 3/145 |
| | | 2/421 |
| 2010/0229286 A1 | 9/2010 | Ahlgren et al. |
| 2012/0144565 A1 | 6/2012 | Huh |
| 2013/0239303 A1* | 9/2013 | Cotterman ............. A42B 3/324 |
| | | 2/417 |
| 2016/0074230 A1* | 3/2016 | Sernfält ................ A42B 3/225 |
| | | 2/8.3 |
| 2016/0262484 A1* | 9/2016 | Huh ........................ A42B 3/14 |
| 2017/0251745 A1 | 9/2017 | Argul |
| 2018/0042330 A1 | 2/2018 | Wu |
| 2018/0042774 A1 | 2/2018 | Wu |
| 2021/0153594 A1 | 5/2021 | Rogers et al. |

\* cited by examiner

HEADGEAR WITH CURVED STRAPS FOR WELDING HELMET

CROSS-REFERENCE TO RELATED APPLICATIONS

This application is a continuation of U.S. patent application Ser. No. 16/442,390, filed Jun. 14, 2019, now U.S. Pat. No. 11,576,454, issued Feb. 14, 2023, the disclosure of which is incorporated herein by reference in its entirety.

TECHNICAL FIELD

The present disclosure relates generally to headgear for a welding helmet. More specifically, the present disclosure relates to an improved design for a headgear having curved bands.

BACKGROUND

Welding helmets have become essential devices on welding sites for protecting welders. Welding helmets typically include a helmet shell that can be connected to a headband that is worn on the welder's head. The headgear can include one of a variety of mechanisms to securely mount the headgear to the welder's head.

For example, current iterations of headgear s include band parts that connect to one side of the headgear, go over the welder's head, and connect to the other side of the headgear. These band parts can be flat and stiff, which can have difficulty conforming to the curvature of the welder's head. Being forced to wear headgear comprising flat and stiff band parts can lead to discomfort for the welder, particularly when the welder is required to wear the headgear for an extended period of time in order to complete a welding task. As a result of the extended period of time welding tasks can take to complete, the issue of discomfort for a welder is a significant concern.

In some instances, the discomfort can be significant enough to negatively impact the welder while performing his or her tasks. For example, the discomfort can prevent a wearer from performing his or her tasks as efficiently or effectively as needed. In addition, the discomfort can lead to safety concerns. Discomfort can lead to diminished concentration, increasing the potential of exposure to harmful heat and sparks.

SUMMARY

Embodiments of the present disclosure include a headgear for a welding helmet and a welding helmet including a headgear.

In one embodiment, a headgear for a helmet includes a front band; a back band; and an intermediate band comprising a plurality of intermediate band parts arranged between the front band and the back band, the plurality of intermediate band parts comprising: a first pair of band parts having a circular shape, the band parts of the first pair of band parts extending from and connecting on a first side of the headgear, a second pair of band parts having a circular shape, the band parts of the second pair of band parts extending from and connecting on a second side of the headgear, a first cross band part intersecting with and extending from the connection of the first pair of band parts, and a second cross band part intersecting with and extending from the connection of the second pair of band parts, the second cross band part detachably couplable with the first cross band part.

In another embodiment, a helmet includes a headgear. The headgear includes a front band; a back band; and an intermediate band comprising a plurality of intermediate band parts arranged between the front band and the back band, the plurality of intermediate band parts comprising: a first pair of band parts having a circular shape, the band parts of the first pair of band parts extending from and connecting on a first side of the headgear, a second pair of band parts having a circular shape, the band parts of the second pair of band parts extending from and connecting on a second side of the headgear, a first cross band part intersecting with and extending from the connection of the first pair of band parts, and a second cross band part intersecting with and extending from the connection of the second pair of band parts, the second cross band part detachably couplable with the first cross band part.

In another embodiment, a headgear for a helmet includes a front band; a back band; and an intermediate band comprising a plurality of intermediate band parts arranged between the front band and the back band, the plurality of intermediate band parts comprising a first pair of band parts having a circular shape, the band parts of the first pair of band parts extending from and connecting on a first side of the headgear, a second pair of band parts having a circular shape, the band parts of the second pair of band parts extending from and connecting on a second side of the headgear, a first cross band part intersecting with and extending from the connection of the first pair of band parts and comprising a buckle, a first portion, and a second portion, and a second cross band part intersecting with and extending from the connection of the second pair of band parts, the second cross band part detachably couplable with the first cross band part and configured to be inserted through the buckle to cause a first portion of the second cross band part, that is received through the buckle, to overlap with of the second portion of the first cross band part; and a second portion of the second cross band part, that is not received through the buckle, to overlap with the first portion of the first cross band part.

Before undertaking the DETAILED DESCRIPTION below, it may be advantageous to set forth definitions of certain words and phrases used throughout the present disclosure. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Definitions for other certain words and phrases are provided throughout the present disclosure. Those of ordinary skill in the art should understand that in many if not most instances, such definitions apply to prior as well as future uses of such defined words and phrases.

BRIEF DESCRIPTION OF THE DRAWINGS

For a more complete understanding of this disclosure and its advantages, reference is now made to the following description, taken in conjunction with the accompanying drawings, in which like reference numerals represent like parts.

DETAILED DESCRIPTION

FIGS. 1 through 6, discussed below, and the various embodiments used to describe the principles of the present disclosure are by way of illustration only and should not be construed in any way to limit the scope of the disclosure. Those skilled in the art will understand that the principles of the present disclosure may be implemented in any suitably arranged headgear.

Figure 1:
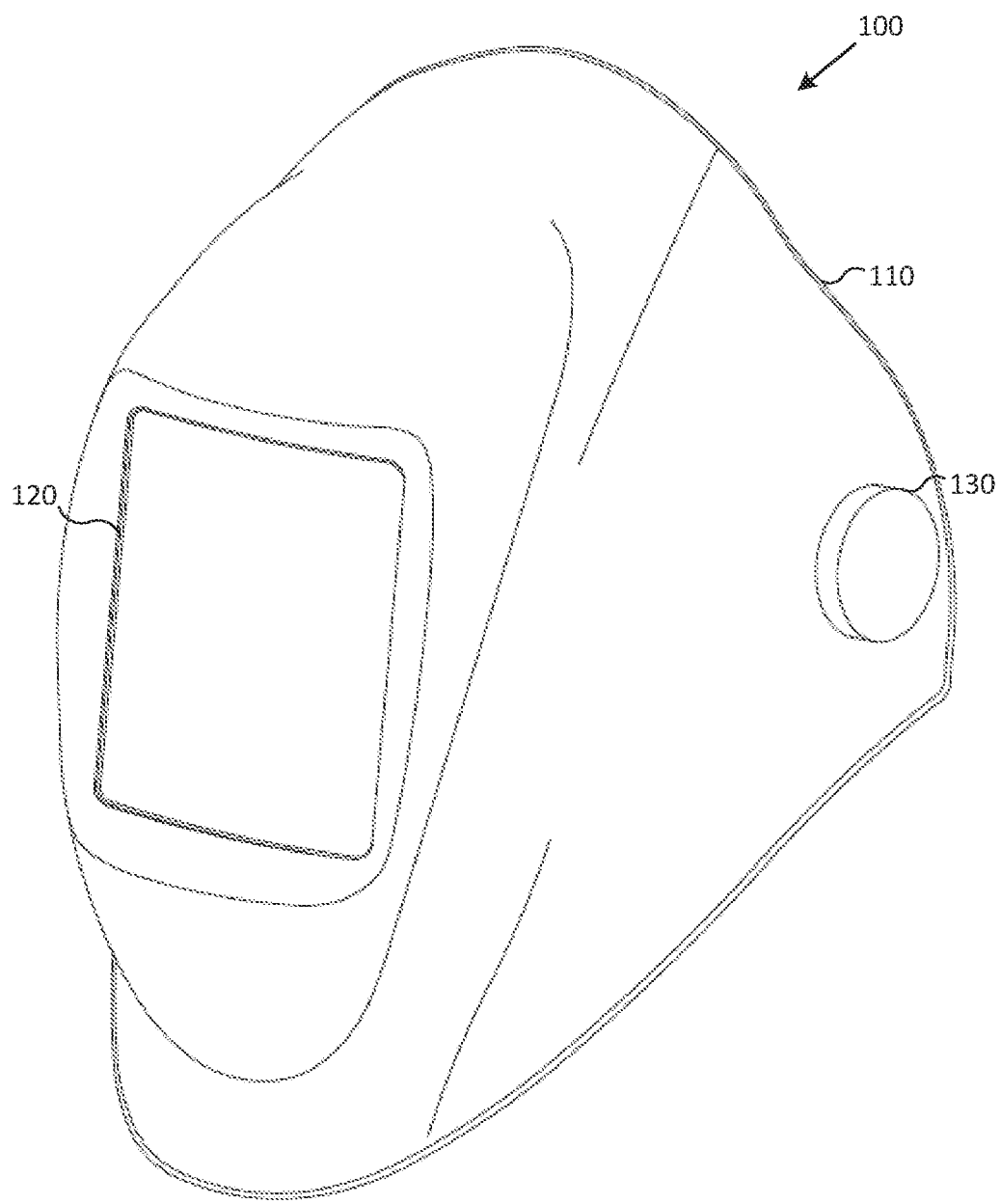
FIG. 1 illustrates a helmet according to various embodiments of the present disclosure.

FIG. 1 illustrates a welding helmet according to various embodiments of the present disclosure. The welding helmet 100 includes a mask 110. In some embodiments, the welding helmet 100 can include a window 120. The present disclosure should not be construed as limiting, and any suitable welding helmet can be utilized.

The mask 110 includes a housing for the window 120 and an attachment structure 130. The attachment structure 130 can be the attachment point for a headgear (for example, the headgear 300 in FIG. 3) or a hard hat. For example, the attachment structure 130 can be a knob that serves as the attachment point for the headgear to the mask 110 by attaching to a prong on the headgear (for example, the prong 380 illustrated in FIGS. 3 and 4 and described below). The mask 110 can comprise any suitable material, for example a plastic or nylon material. In various embodiments, the mask can be referred to as a housing or a helmet housing.

The window 120 can be any suitable type of window that protects the operator's eyes while allowing the operator to work. The window can be made of any suitable type of material to protect the operator's eyes, such as a tinted glass or plastic material. In some embodiments, the window 120 can include an auto-darkening type filter that is transparent before welding-arc ignition and becomes opaque in response to welding-arc ignition. In other embodiments, the welding helmet 100 does not include the window 120 and instead the welding helmet 100 must be raised above the operator's head to provide for viewing of the welding surface.

Figure 2:
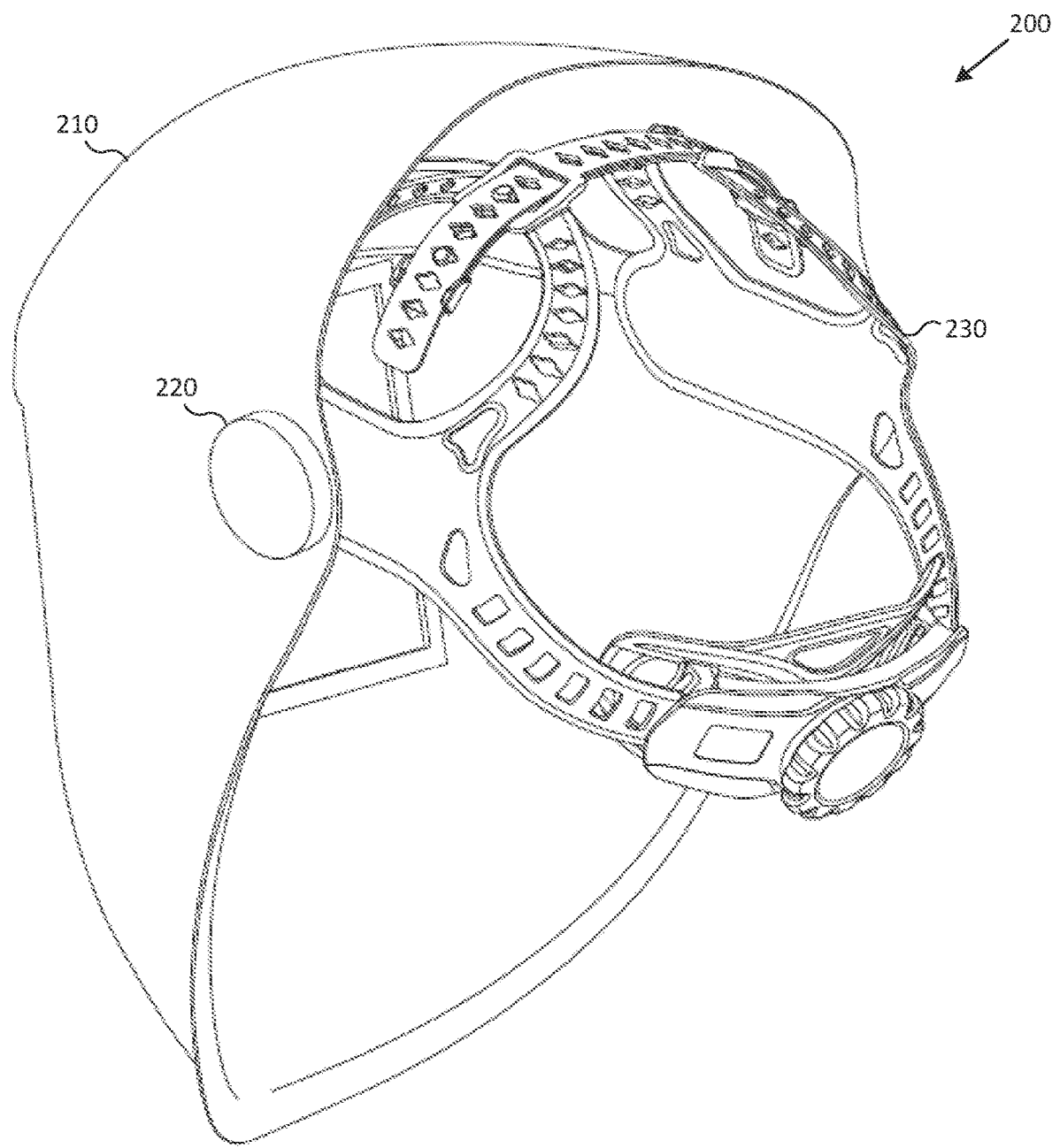
FIG. 2 illustrates a helmet and headgear according to various embodiments of the present disclosure.

FIG. 2 illustrates a welding helmet and headgear according to various embodiments of the present disclosure. The welding helmet 200 can be the welding helmet 100 or any other suitable welding helmet. As shown in FIG. 2, the welding helmet 200 can include a mask 210 that includes an attachment structure 220 to connect to the headgear 230. The attachment structure 220 can be the attachment structure 130 illustrated in FIG. 1. The headgear 230 can be the headgear 300 illustrated in FIG. 3 and described below.

The headgear 230 is designed to be worn on the operator's head and provide a connection point for the mask 210. In many welding situations, the combination of the mask 210 and headgear 230 is worn for extended periods of time in order to successfully perform welding operations. Because of the weight of the mask 210 and the extended periods of time the mask 210 is worn for, the comfort of the headgear 230 is a significant concern. If the headgear 230 is uncomfortable, the operator may require more frequent breaks, which prolongs the welding operations and time spent wearing the mask 210. To that end, the present disclosure includes a headgear 230 that increases the comfort of the operator while wearing the mask 210 and performing welding operations.

In order to improve the comfort of the wearer, the present disclosure includes a headgear that includes circular band parts that connect to both sides of the headgear. The circular band parts conform to the curvature of the wearer's head, resulting in increased comfort especially when the headgear is worn for extended periods of time. This can reduce the negative impacts of discomfort to the wearer and enable the wearer to perform his or her tasks more efficiently or effectively.

Figure 3:
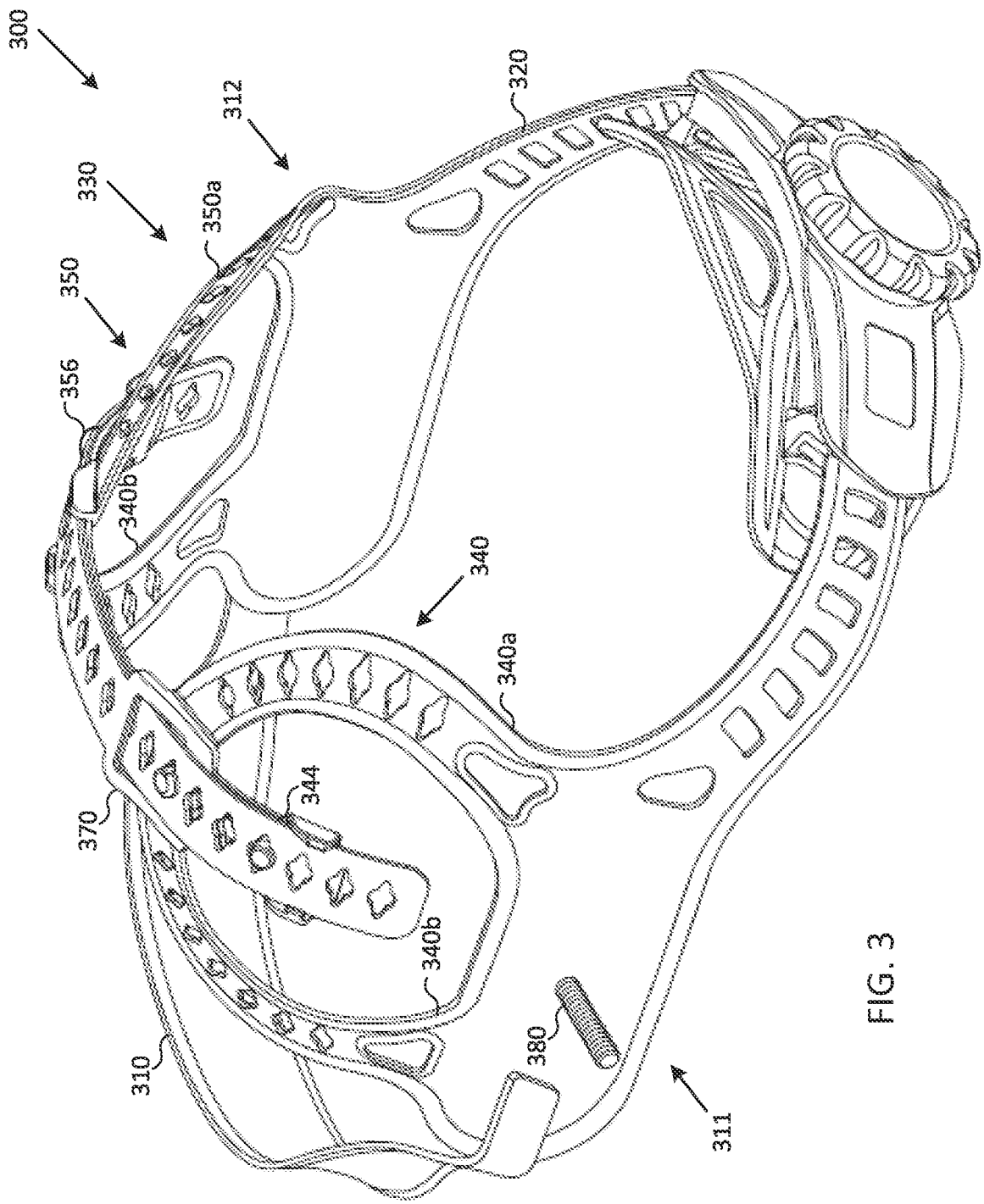
FIG. 3 illustrates a rear perspective view of a headgear according to various embodiments of the present disclosure.
Figure 4:
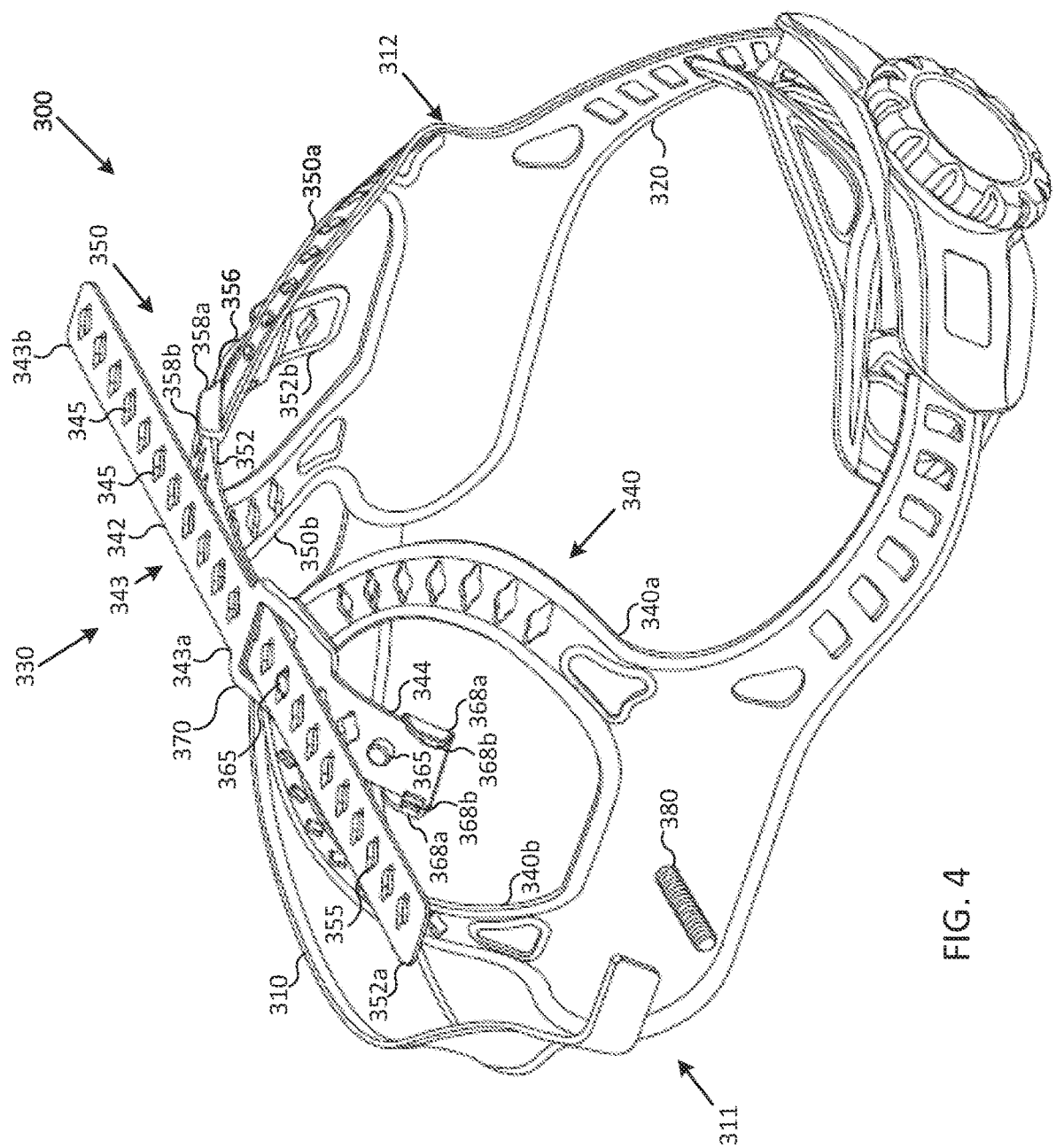
FIG. 4 illustrates a rear perspective view of a headgear according to various embodiments of the present disclosure.

FIGS. 3 and 4 each illustrate a rear perspective view of a headgear according to various embodiments of the present disclosure. The headgear 300 can be the headgear 230 illustrated in FIG. 2.

The headgear 300 includes a front band 310, a back band 320, and an intermediate band 330 arranged between the front band 310 and the back band 320. When taken together, the front band 310, the back band 320, and the intermediate band 330 secure the headgear 300 on an operator's head when the mask 210 is being worn by the operator.

The front band 310 is designed to secure the headgear 300 to an operator's forehead. The front band 310 can be configured to allow a cover or cushion to be attached in order to make the headgear 300 more comfortable for an operator. In some embodiments, the front band 310 is adjustable to provide a secure and comfortable fit for the operator.

The back band 320 is designed to secure the headgear 300 to the rear portion of an operator's head. In some embodiments, the back band 320 can be adjustable to provide a secure and comfortable fit for the operator. In some embodiments, the back band 320 can be configured to allow a cover or cushion to be attached in order to make the back band 320 more comfortable for an operator.

The intermediate band 330 includes a plurality of intermediate band parts. The plurality of intermediate band parts include a first pair of band parts 340a 340b, a first cross band part 342, a second pair of band parts 350a, 350b, and a second cross band part 352. The first pair of band parts 340 have a circular shape and extend from and connect on a first side 311 of the headgear 300. The first cross band part 342 includes a first portion 343 that includes a first end 343a, a second end 343b, and a plurality of notches 345. The first end 342a of the first cross band part 342 connects the first cross band part 342 to the first pair of band parts 340. The first cross band part 342 further includes a second portion 344.

The second pair of bands parts 350 have a circular shape and extend from and connect on a second side 312 of the headgear 300. The second cross band part 352 includes a first end 352a, a second end 352b, a plurality of notches 355, a tab 356, and rails 358. The second end 352b of the second cross band part 352 connects the second cross band part 352 to the second pair of band parts 350.

In the present disclosure, portions of the intermediate band 330 are described as having a circular shape. The circular shape is not limited to a complete or geometrically perfect circle but is circular in nature and can be understood to include that portions of the intermediate band 330 to have a shape that is round, ovular, a partial circle, or any other suitable shape that has a curvature.

The tab 356 is an extended member that projects from the second cross band part 352. The tab 356 can be of any suitable length to extend through one of the plurality of notches 345 of the first cross band part 342.

The rails 358 include first portions 358a and second portions 358b. The first portions 358a vertically project from the second cross band part 352. For example, the first portions 358a vertically project from sides of the second cross band part 352 at least a distance that is greater than a thickness of the first cross band part 342. The second portions 358b horizontally project from the first portions 358a toward one another at a point that is distal to the connection of the first portion 358a to the second cross band part 352. The second portions 358b are configured to guide the first cross band part 342 and keep the first cross band part 342 aligned with the second cross band part 352. For example, the second portions 358b guide the portions of the first and second cross band parts 342, 352 that extend across the headgear 300 to overlap with corresponding portions first and second cross band parts 342, 352, respectively.

The second portion 344 of the first cross band part 342 extends away from the first portion 343 of the first cross band part 342. In some embodiments, the second portion 344 can extend from the first pair of band parts 340 at the portion of the first pair of band parts 340 that comprises the buckle 370. The second portion 344 can have a length that is less than the length of the first portion 343 of the first cross band part 342. The second portion 344 includes a tab 365 and rails 368.

The tab 365 is an extended member that projects from the second portion 344. The tab 365 can be of any suitable length to extend through one of the plurality of notches 355 of the second cross band part 352.

The rails 368 include first rail portions 368a and second rail portions 368b. The first rail portions 368a vertically project from the second portion 344. For example, the first rail portions 368a vertically project from sides of the second portion 344 at least a distance that is greater than a thickness of the second cross band part 352. The second rail portions 368b horizontally project from the first rail portions 368a toward one another at a point that is distal to the connection of the first rail portion 368a to the second portion 344. The second rail portions 368b are configured to guide the second cross band part 352 and keep the second cross band part 352 aligned with the second portion 344.

The first cross band part 342 can be detachably coupled to the second cross band part 352. Coupling together the first cross band part 342 and the second cross band part 352 serves as a connection for the first pair of band parts 340 and the second pair of band parts 350. The first cross band part 342 can be detachably coupled to the second cross band part 352 through the use of a buckle 370, the plurality of notches 345, and the tabs 356, 365.

The first end 343a of the first portion 343 is connected to the buckle 370. The buckle 370 includes an opening (for example, the opening 521 illustrated in FIGS. 5A-5B) that is configured to receive the second cross band part 352. When the first end 352a of the second cross band part 352 is inserted through the opening of the buckle 370, the first end 352a of the second cross band part 352 is positioned above the second portion 344 and the second end 352b of the second cross band part 352 is positioned below the second end 343b of the first portion 343 of the first cross band part 342.

Although the terms above and below are used herein, these terms merely provide perspective and should not be construed as limiting. For example, the terms above and below are used to describe the orientation of the headgear 300 as illustrated in FIGS. 3 and 4. Embodiments where the first end 352a of the second cross band part 352 is positioned below the second portion 344 and the second end 352b of the second cross band part 352 is positioned above the second end 343b of the first portion 343 of the first cross band part 342 are also possible. For example, the tabs 356, 365 and rails 358, 368 can be located on the opposite sides of the second cross band part 352 and second portion 344. In this embodiment, based on the headgear 300 being viewed from the perspective of FIGS. 3 and 4, the first end 352a of the second cross band part 352 is positioned below the second portion 344 and the second end 352b of the second cross band part 352 is positioned above the second end 343b of the first portion 343 of the first cross band part 342.

The first cross band part 342 and the second cross band part 352 are secured together by the combination of the plurality of notches 345, the plurality of notches 355, the tab 356, the rails 358, the second portion 344, the tab 365, the rails 368, and the buckle 370. More particularly, the first end 352a of the second cross band part 352 is received through the opening of the buckle 370 and secured to the second portion 344. At or around the same time, the second end 343b of the first portion 343 of the first cross band part 342 is secured to the second end 352b of the second cross band part 352.

As discussed above, the first end 352a of the second cross band part 352 can be inserted through the opening of the buckle 370. After being inserted through the opening of the buckle 370, the first end 352a is inserted under the second rail portion 368b of the rails 368 of the second portion 344 to align the second cross band part 352 with the second portion 344. After the second cross band part 352 is aligned with the second portion 344, the tab 365 is inserted through one of the plurality of notches 355 on the second cross band part 352. The tab 365 being inserted through one of the plurality of notches 355, in combination with the alignment of the second cross band part 352 with second portion 344, determines a distance between the first pair of band parts 340 and the second pair of band parts 350. The distance between the first pair of band parts 340 and the second pair of band parts 350 is determined based on which of the plurality of notches 355 the tab 365 is inserted through. For example, inserting the tab 365 through the one of the plurality of notches 355 that is nearest to the first end 352a will result in a greater distance between the first pair of band parts 340 and the second pair of band parts 350 than if the tab 365 is inserted through the one of the plurality of notches 355 that is further from the first end 352a. The tab 365 being inserted through one of the plurality of notches 355 further restricts movement of the second cross band part 352. By restricting movement of the second cross band part 352, a secure fit of the headgear 300 to the operator's head can be improved.

At or around the same time the second cross band part 352 is secured to the second portion 344, the first cross band part 342 is secured to the second cross band part 352. The second end 343b of the first portion 343 of the first cross band part 342 is inserted under the second portion 358b of the rails 358 to align the first cross band part 342 with the second cross band part 352. After the first cross band part 342 is aligned with the second cross band part 352, the tab 356 is inserted through one of the plurality of notches 345 on the first cross band part 342. The tab 356 being inserted through one of the plurality of notches 345, in combination with the alignment of the first cross band part 342 with the second cross band part 352, determines a distance between the first pair of band parts 340 and the second pair of band parts 350. The distance between the first pair of band parts 340 and the second pair of band parts 350 is determined based on which of the plurality of notches 345 the tab 356 is inserted through. For example, inserting the tab 356 through one of the plurality of notches 345 that is nearest to the second end 343b will result in a greater distance between the first pair of band parts 340 and the second pair of band parts 350 than if the tab 356 is inserted through one of the plurality of notches 345 that is further from the second end 343b. The tab 356 being inserted through one of the plurality of notches 345 further restricts movement of the first cross band part 342. By restricting movement of the first cross band part 342, a secure fit of the headgear 300 to the operator's head can be improved.

Although depicted herein as an ordered series of steps where the second cross band part 352 is secured to the second portion 344 followed by the first cross band part 342 being secured to the second cross band part 352, this description should not be construed as limiting. Various embodiments are possible. For example, the first cross band part 342 can be secured to the second cross band part 352 prior to the second cross band part 352 being secured to the second portion 344. In some embodiments, depending on the size of the operator's head, the tab 365 can be inserted through one of the plurality of notches 355 without the second cross band part 352 being inserted under the rails 368 if an insufficient amount of the second cross band part 352 is extended through the opening of the buckle 370 to reach the rails 368. In some embodiments, the headgear 300 can include more than one tab 356 and/or more than one tab 365 to further secure the second cross band part 352 to either the first cross band part 342 or the second portion 344, respectively. In some embodiments, the headgear 300 can include more than one set of rails 358 and/or more than one set of rails 368 to further secure the second cross band part 352 to either the first cross band part 342 or the second portion 344, respectively.

The headgear 300 further includes a prong 380 on each of the first side 311 and the second side 312. The prong 380 is configured to be inserted into an attachment structure on a helmet, for example the attachment structure 130, to secure the headgear to the welding helmet 100. However, this description should not be construed as limiting. The prong 380 can take a variety of forms, such as a prong, a bolt, or any other suitable structure to secure the headgear to the welding helmet 100.

The prong 380 is included on each of the first side 311 and the second side 312. For example, on the first side 311, the prong 380 is located proximate to the first pair of band parts 340 and opposite from the buckle 370. Although not illustrated in FIGS. 3 and 4, on the second side 312 a prong 380 is located proximate to the second pair of band parts 350.

Figure 5A:
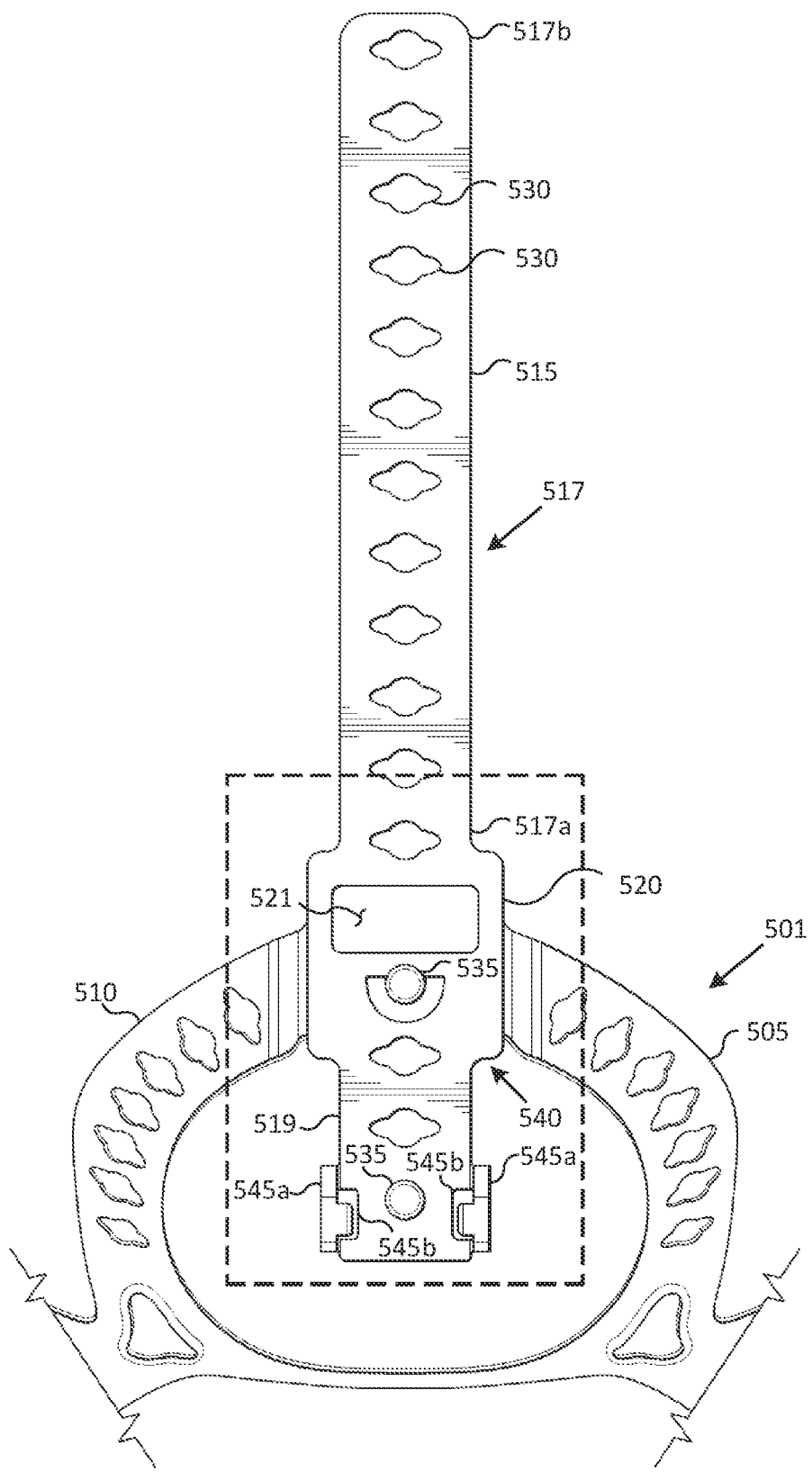
FIGS. 5A and 5B illustrate a headgear according to various embodiments of the present disclosure.
Figure 5B:
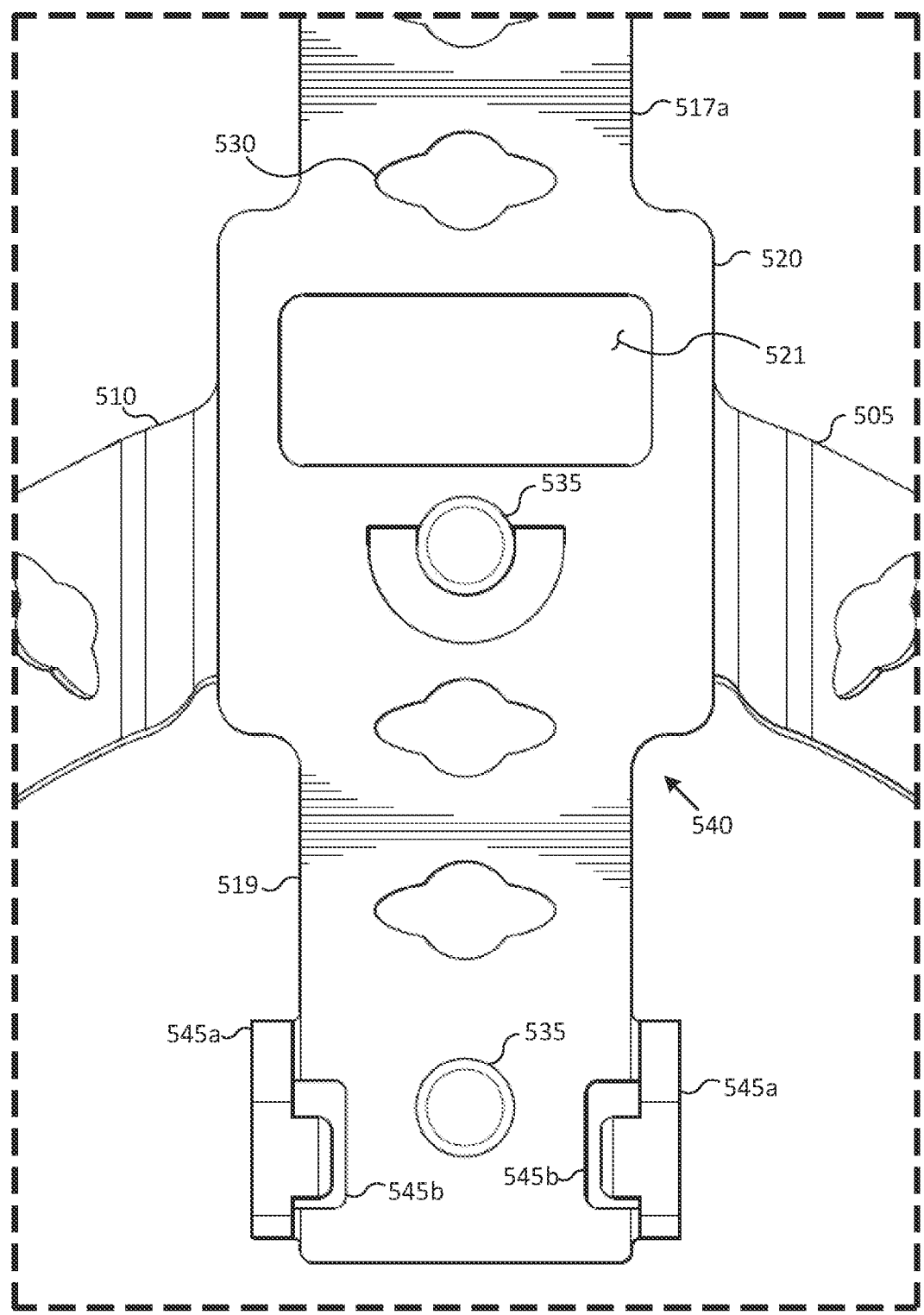

FIGS. 5A and 5B illustrate a headgear according to various embodiments of the present disclosure. In particular, FIGS. 5A and 5B illustrate a first pair of band parts 501, a first cross band part 515, and a buckle 520. The first pair of band parts 501 can be the first pair of band parts 340. The first cross band part 515 can be the first cross band part 342. The buckle 520 can be the buckle 370.

The first pair of band parts 501 have a circular shape and include a first part 505 and a second part 510 extending from and connecting on a first side of a headgear, for example the headgear 300. The first part 505 and the second part 510 are each curved to conform to the curvature of a wearer's head. The first part 505 and the second part 510 can be joined together at a junction 540 that is proximate to the buckle 520. In some embodiments, the first part 505 and the second part 510 can be two separate straps that are joined at the junction 540. In other embodiments, the first part 505 and the second part 510 can be a single strap with the first part 505 being a first portion of the strap and the second part 510 being a second portion of the strap.

The first cross band part 515 includes a first portion 517 and a second portion 519. The first portion 517 can be the first portion 343. The second portion 519 can be the second portion 344. The first portion 517 includes a first end 517a and a second end 517b. The first end 517a is the portion of the first cross band part 515 that is attached to the buckle 520. The second end 517b is the portion of the first cross band part 515 that is distal from the buckle 520 and is configured to be secured to another portion of the headgear. For example, the second end 517b can be secured to the second end 615b of the second cross band part 615 illustrated in FIG. 6. The first cross band part 515 further includes a plurality of notches 530 that are configured to receive a tab, for example the tab 625 illustrated in FIG. 6.

FIG. 5B is a magnified version of the cutaway illustrated in FIG. 5A. As shown in FIG. 5B, the first part 505 and the second part 510 are joined together at the junction 540. The first cross band part 515 is attached to the first pair of band parts 501 at the junction 540. The second portion 519 is joined to each of the first part 505 and the second part 510 at the junction 540 opposite from the first cross band part 515. The second portion 519 is used to secure another cross band part, for example the second cross band part 615 illustrated in FIG. 6.

The buckle 520 is located between the first portion 517 and the second portion 519 at the junction 540. The buckle 520 includes an opening 521. The opening 521 is a space that is configured to receive a band part, for example the second cross band part 615 illustrated in FIG. 6.

The second portion 519 further includes a tab 535 and rails 545. The tab 535 can be the tab 365. The rails 545 can be the rails 368. The tab 535 is configured to be inserted through one of a plurality of notches on a complimentary cross band part, for example one of the plurality of notches 620 on the second cross band part 615 illustrated in FIG. 6. In some embodiments, the second portion 519 can include more than one tab 535. For example, as illustrated in FIG. 5B, the second portion 519 can include more than one tab 535 to further secure the complimentary cross band part.

The rails 545 are configured to receive a cross band part under the rails 545 to align the received cross band part with the second portion 519. The rails 545 include first rail portions 545a and second rail portions 545b. The first rail portions 545a vertically project from the second portion 519. For example, the first rail portions 545a vertically project from sides of the second portion 519 at least a distance that is greater than a thickness of the second cross band part 615. The second rail portions 545b horizontally project from the first rail portions 545a toward one another at a point that is distal to the connection of the first rail portion 545a to the second portion 519. The second rail portions 545b are configured to guide the second cross band part 615 and keep the second cross band part 615 aligned with the second portion 519.

Figure 6:
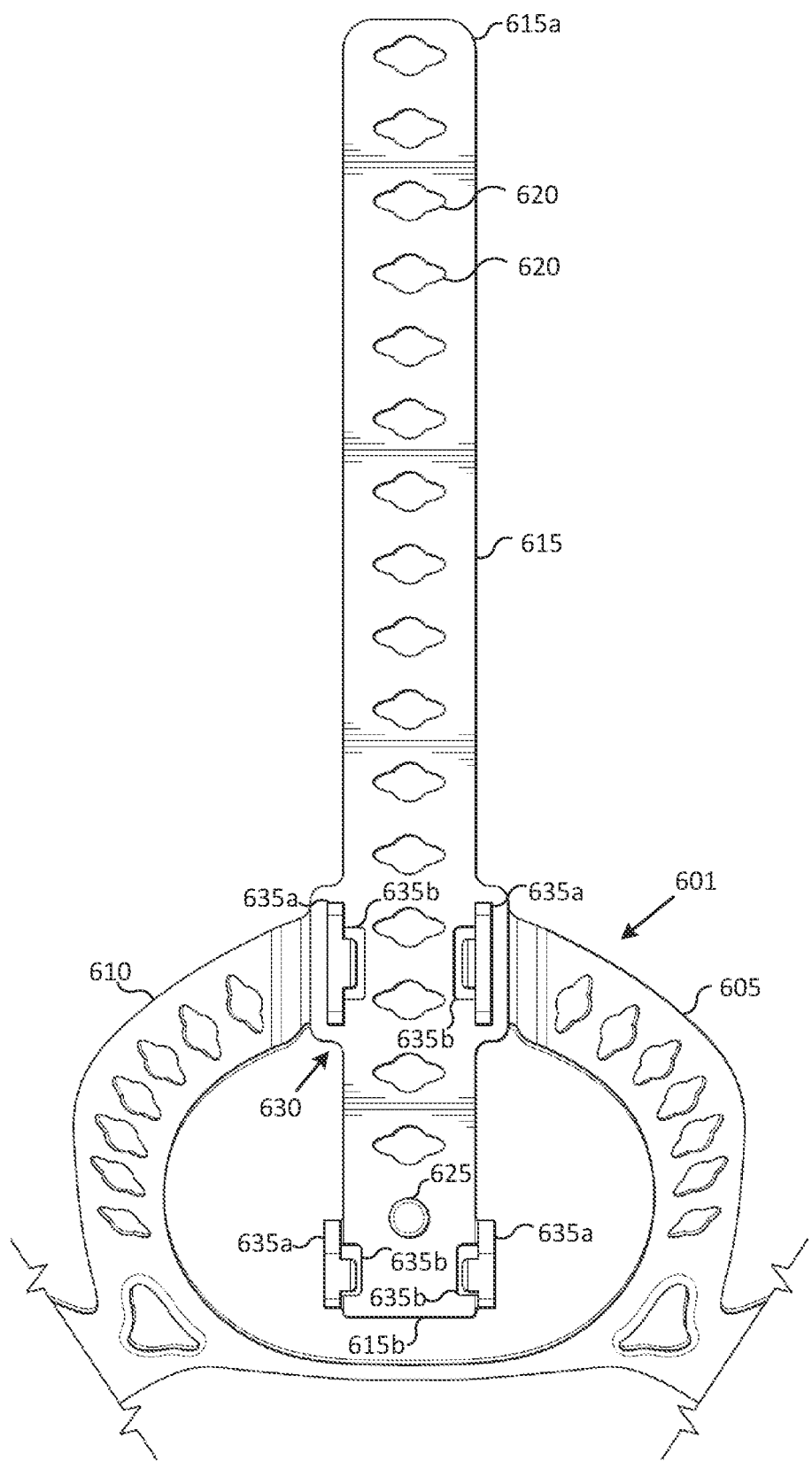
FIG. 6 illustrates a headgear according to various embodiments of the present disclosure.

FIG. 6 illustrates a headgear according to various embodiments of the present disclosure. In particular, FIG. 6 illustrates a second pair of band parts 601 and a second cross band part 615. The second pair of band parts 601 can be the second pair of band parts 350. The second cross band part 615 can be the second cross band part 352.

The second pair of band parts 601 have a circular shape and include a third part 605 and a fourth part 610 extending from and connecting on a second side of a headgear, for example the headgear 300. The third part 605 and the fourth part 610 are each curved to fit the curvature of a wearer's head. The third part 605 and the fourth part 610 can be joined together at a junction 630. In some embodiments, the third part 605 and the fourth part 610 can be two separate straps that are joined at the junction 630. In other embodiments, the third part 605 and the fourth part 610 can be a single strap with the third part 605 being a first portion of the strap and the fourth part 610 being a second portion of the strap.

In some embodiments, the third part 605 and the fourth part 610 are designed to be complimentary to the first part 505 and the second part 510. In other words, each of (i) the first part 505 and the second part 510 and (ii) the third part 605 and the fourth part 610 are designed with a similar size and curvature to provide an increased level of comfort for the wearer who wears the headgear that includes both of the first pair of band parts 501 and the second pair of band parts 601.

The second cross band part 615 includes a first end 615a and a second end 615b. The second cross band part 615 is attached to the second pair of band parts 601 at the junction 630. The first end 615a is configured to be received through a buckle on a complimentary cross band part, for example the buckle 520 on the first pair of band parts 501. The second end 615b includes a tab 625 and rails 635. The tab 625 can be the tab 365. The rails 635 can be the rails 368. The tab 625 is configured to secure the second cross band part 615 to a complimentary cross band part, for example the first cross band part 515.

The rails 635 are configured to receive a cross band part under the rails 635 to align the received cross band part with the second cross band part 615. The rails 635 include first rail portions 635a and second rail portions 635b. The first rail portions 635a vertically project from the second cross band part 615. For example, the first rail portions 635a vertically project from sides of the second cross band part 615 at least a distance that is greater than a thickness of the first cross band part 515. The second rail portions 635b horizontally project from the first rail portions 635a toward one another at a point that is distal to the connection of the first rail portion 635a to the second cross band part 615. The second rail portions 635b are configured to guide the first cross band part 515 and keep the first cross band part 515 aligned with the second cross band part 615.

In some embodiments, the second cross band part 615 can include a plurality of markings to assist in an operator in achieving a secure fit of the headgear according to the embodiments described in FIGS. 5A-6. For example, the second cross band part 615 can include sequentially ordered numerals, each corresponding to one of the plurality of notches 620. The numerals can assist an operator to insert the tab 535 through the correct one of the plurality of notches 620. The numerals can be arranged such that the lowest numeral is associated with either the one of the plurality of notches 620 that is proximate to the first end 615a or the one of the plurality of notches 620 that is proximate to the second end 615b.

A complete headgear can include various embodiments of the present disclosure that are incorporated together. For example, the first pair of band parts 501, first cross band part 515, second portion 519, second pair of band parts 601, and second cross band part 615 can be combined to form the intermediate band 330 of the headgear 300 that is then worn with the welding helmet 100. The first end 615a of the second cross band part 615 can be inserted through the opening 521 of the buckle 520 and aligned above the second portion 519. Once the first end 615a of the second cross band part 615 is inserted through the opening 521 of the buckle 520, the second end 517b of the first cross band part 515 is aligned above the second end 615b of the second cross band part 615.

Once the first cross band part 515 and second cross band part 615 are aligned, the first cross band part 515 and second cross band part 615 are secured together via the plurality of notches 530, tab 535, rails 545, plurality of notches 620, tab 625, and rails 635. The first end 615a of the second cross band part 615 can be inserted under the rails 545 and adjusted to the correct length. When the length is properly adjusted, the tab 535 can be inserted through the corresponding one of the plurality of notches 620. At or around the same time, the second end 517b of the first cross band part 515 can be inserted under the rails 635. The tab 625 can then be inserted through the corresponding one of the plurality of notches 530.

The embodiments described in the present disclosure should not be construed as limiting. Various embodiments are possible. In some embodiments, the first cross band part includes a first portion extending toward the second pair of band parts and a second portion extending away from the second pair of band parts when the second cross band part is coupled with the first cross band part. In some embodiments, the first cross band part comprises a buckle that is configured to receive the second cross band part and cause a first portion of the second cross band part, that is received through the buckle, to overlap with the first cross band part.

In some embodiments, the first cross band part includes a first portion extending toward the second pair of band parts and a second portion extending away from the second pair of band parts when the second cross band part is coupled with the first cross band part.

In some embodiments, the first cross band part further comprises a plurality of notches. In some embodiments, the second portion of the second cross band part further comprises a tab configured to extend through one of the plurality of notches.

In some embodiments, the second cross band part further comprises a plurality of notches. In some embodiments, the extending band part further comprises a tab configured to extend through one of the plurality of notches.

In some embodiments, the first cross band part includes a buckle that is configured to receive the second cross band part and cause a first portion of the second cross band part, that is received through the buckle, to overlap with the first band part, the first and second cross band parts include first and second rails, respectively, the first and second rails are configured to guide portions of the first and second cross band parts that extend across the headgear to overlap with corresponding portions first and second cross band parts, respectively, the first and second cross band parts include a plurality of notches, the first and second cross band parts include first and second tabs, respectively, the first and second tabs are disposed adjacent to the first and second rails, respectively, and the first and second tabs are configured to couple with respective notches of the portions of the first and second cross band parts that extend across the headgear and, in combination with the first and second rails, respectively, hold the first and second cross band parts adjacent to and overlapped with each other so as to form the intermediate band.

In some embodiments, a headgear for a welding helmet comprises a front band; a back band; and an intermediate band comprising a plurality of intermediate band parts arranged between the front band and the back band, the plurality of intermediate band parts comprising a first pair of band parts having a circular shape, the band parts of the first pair of band parts extending from and connecting on a first side of the headgear, a second pair of band parts having a circular shape, the band parts of the second pair of band parts extending from and connecting on a second side of the headgear, a first cross band part intersecting with and extending from the connection of the first pair of band parts and comprising a buckle, a first portion, and a second portion, and a second cross band part intersecting with and extending from the connection of the second pair of band parts, the second cross band part detachably couplable with the first cross band part and configured to be inserted through the buckle to cause: a first portion of the second cross band part, that is received through the buckle, to overlap with of the second portion of the first cross band part; and a second portion of the second cross band part, that is not received through the buckle, to overlap with the first portion of the first cross band part.

In some embodiments, the first cross band part further comprises a plurality of notches, and the second portion of the second cross band part further comprises a tab configured to extend through one of the plurality of notches.

In some embodiments, the second cross band part further comprises a plurality of notches, and the second portion of the first cross band part further comprises a tab configured to extend through one of the plurality of notches.

In some embodiments, the first and second cross band parts include first and second rails, respectively; the first and second rails are configured to guide portions of the first and second cross band parts that extend across the headgear to overlap with corresponding portions first and second cross band parts, respectively; the first and second cross band parts include a plurality of notches; the first and second cross band parts include first and second tabs, respectively; the first and second tabs are disposed adjacent to the first and second rails, respectively; and the first and second tabs are configured to couple with respective notches of the portions of the first and second cross band parts that extend across the headgear and, in combination with the first and second rails, respectively, hold the first and second cross band parts adjacent to and overlapped with each other so as to form the intermediate band.

None of the description in this application should be read as implying that any particular element, step, or function is an essential element that must be included in the claim scope. Moreover, none of the claims is intended to invoke 35 U.S.C. § 112(f) unless the exact words "means for" are followed by a participle.

What is claimed is:

1. A headgear comprising:
   a front band;
   a back band; and
   an intermediate band that extends from a first side of the headgear to a second side of the headgear across a top of the headgear between the front band and the back band, the intermediate band comprising a plurality of intermediate band parts comprising:
   a first pair of band parts having a circular shape, a first band part of the first pair of band parts extending from a different location of the first side of the headgear than a second band part of the first pair of band parts, the first pair of band parts forming a connection, the first pair of band parts comprising a buckle at the connection,
   a second pair of band parts having a circular shape, a first band part of the second pair of band parts extending from a different location of the second side of the headgear than a second band part of the second pair of band parts, the second pair of band parts connecting on the second side of the headgear,
   a first cross band part intersecting with and extending from the buckle at the connection of the first pair of band parts, and
   a second cross band part intersecting with and extending from the connection of the second pair of band parts, the second cross band part detachably couplable with the first cross band part at the connection of the first pair of band parts via the buckle,
   wherein the front band, the back band, and the intermediate band extend in directions, respectively, that are parallel to an axis that extends from the first side of the headgear to the second side of the headgear, and
   wherein extension of the first and second pairs of band parts from the back band on the first and second sides of the headgear, respectively, is first outwardly relative to the axis and then inwardly toward the axis to form the circular shapes, respectively.

2. The headgear of claim 1, wherein the first cross band part includes a first portion extending toward the second pair of band parts and a second portion extending away from the second pair of band parts when the second cross band part is coupled with the first cross band part.

3. The headgear of claim 2, wherein the buckle is configured to receive the second cross band part and cause a first portion of the second cross band part, that is received through the buckle, to overlap with the first cross band part.

4. The headgear of claim 3, wherein the first cross band part comprises a plurality of notches.

5. The headgear of claim 4, wherein the second cross band part comprises a tab configured to extend through one of the plurality of notches.

6. The headgear of claim 5, wherein the second cross band part further comprises a plurality of notches.

7. The headgear of claim 6, wherein the second portion of the first cross band part further comprises a tab configured to extend through one of the plurality of notches of the second cross band part.

8. The headgear of claim 1, wherein:
   the buckle is configured to receive the second cross band part and cause a first portion of the second cross band part, that is received through the buckle, to overlap with the first cross band part;
   the first and second cross band parts include first and second rails, respectively;
   the first and second rails are configured to guide portions of the first and second cross band parts that extend across the headgear to overlap with corresponding portions first and second cross band parts, respectively;
   the first and second cross band parts include a plurality of notches;
   the first and second cross band parts include first and second tabs, respectively;
   the first and second tabs are disposed adjacent to the first and second rails, respectively; and
   the first and second tabs are configured to couple with respective notches of the portions of the first and second cross band parts that extend across the headgear and, in combination with the first and second rails, respectively, hold the first and second cross band parts adjacent to and overlapped with each other so as to form the intermediate band.

9. A helmet comprising:
a mask; and
a headgear operably connected to the mask, the headgear comprising:
   a front band;
   a back band; and
   an intermediate band that extends from a first side of the headgear to a second side of the headgear across a top of the headgear between the front band and the back band, the intermediate band comprising a plurality of intermediate band parts comprising:
      a first pair of band parts having a circular shape, a first band part of the first pair of band parts extending from a different location of the first side of the headgear than a second band part of the first pair of band parts, the first pair of band parts forming a connection, the first pair of band parts comprising a buckle at the connection,
      a second pair of band parts having a circular shape, a first band part of the second pair of band parts extending from a different location of the second side of the headgear than a second band part of the second pair of band parts, the second pair of band parts connecting on the second side of the headgear,
      a first cross band part intersecting with and extending from the buckle at the connection of the first pair of band parts, and
      a second cross band part intersecting with and extending from the connection of the second pair of band parts, the second cross band part detachably couplable with the first cross band part at the connection of the first pair of band parts via the buckle,
wherein the front band, the back band, and the intermediate band extend in directions, respectively, that are parallel to an axis that extends from the first side of the headgear to the second side of the headgear, and
wherein extension of the first and second pairs of band parts from the back band on the first and second sides of the headgear, respectively, is first outwardly relative to the axis and then inwardly toward the axis to form the circular shapes, respectively.

10. The helmet of claim 9, wherein the first cross band part includes a first portion extending toward the second pair of band parts and a second portion extending away from the second pair of band parts when the second cross band part is coupled with the first cross band part.

11. The helmet of claim 10, wherein the buckle is configured to receive the second cross band part and cause a first portion of the second cross band part, that is received through the buckle, to overlap with the first cross band part.

12. The helmet of claim 11, wherein the first cross band part comprises a plurality of notches.

13. The helmet of claim 12, wherein the second cross band part comprises a tab configured to extend through one of the plurality of notches.

14. The helmet of claim 13, wherein the second cross band part further comprises a plurality of notches.

15. The helmet of claim 14, wherein the second portion of the first cross band part further comprises a tab configured to extend through one of the plurality of notches of the second cross band part.

16. The helmet of claim 9, wherein:
   the buckle is configured to receive the second cross band part and cause a first portion of the second cross band part, that is received through the buckle, to overlap with the first cross band part;
   the first and second cross band parts include first and second rails, respectively;
   the first and second rails are configured to guide portions of the first and second cross band parts that extend across the headgear to overlap with corresponding portions first and second cross band parts, respectively;
   the first and second cross band parts include a plurality of notches;
   the first and second cross band parts include first and second tabs, respectively;
   the first and second tabs are disposed adjacent to the first and second rails, respectively; and
   the first and second tabs are configured to couple with respective notches of the portions of the first and second cross band parts that extend across the headgear and, in combination with the first and second rails, respectively, hold the first and second cross band parts adjacent to and overlapped with each other so as to form the intermediate band.

* * * * *